United States Patent [19]

Noblitt et al.

[11] Patent Number: 5,203,787
[45] Date of Patent: Apr. 20, 1993

[54] SUTURE RETAINING ARRANGEMENT

[75] Inventors: Niles Noblitt, Mountain Lakes, N.J.; Kevin Stone, Warsaw, Ind.

[73] Assignee: Biomet, Inc., Warsaw, Ind.

[21] Appl. No.: 615,353

[22] Filed: Nov. 19, 1990

[51] Int. Cl.⁵ .............................................. A61B 17/00
[52] U.S. Cl. ..................................... 606/232; 606/72; 411/460
[58] Field of Search ................... 606/72, 75, 232; 411/460, 461, 466, 483, 530, 439, 922

[56] References Cited

U.S. PATENT DOCUMENTS

| | | | |
|---|---|---|---|
| 417,805 | 12/1889 | Beaman | 411/460 |
| 1,153,450 | 9/1915 | Schaff | 411/922 |
| 2,846,712 | 8/1958 | Markman | 411/460 |
| 2,913,042 | 11/1959 | Taylor | 411/460 |
| 3,000,009 | 9/1961 | Selstad | 411/460 |
| 3,125,095 | 3/1964 | Kaufman et al. | |
| 4,235,238 | 11/1980 | Ogiu et al. | 606/145 |
| 4,409,974 | 10/1983 | Freedland | 606/72 |
| 4,590,928 | 5/1986 | Hunt et al. | 606/72 |
| 4,632,100 | 12/1986 | Somers et al. | 606/232 |
| 4,683,895 | 8/1987 | Pohndorf | |
| 4,738,255 | 4/1988 | Goble et al. | 606/75 |
| 4,741,330 | 5/1988 | Hayhurst | |
| 4,784,126 | 11/1988 | Hourahane | |
| 4,832,026 | 5/1989 | Jones | 606/232 |
| 4,834,098 | 5/1989 | Jones | |
| 4,898,156 | 2/1990 | Gatturna et al. | 606/72 |
| 4,899,743 | 2/1990 | Nicholson et al. | 606/139 |
| 4,946,468 | 8/1990 | Li | 606/232 |
| 5,007,921 | 4/1991 | Brown | 606/221 |
| 5,030,224 | 7/1991 | Wright et al. | 606/213 |
| 5,037,422 | 8/1991 | Hayhurst et al. | 606/72 |
| 5,041,129 | 8/1991 | Hayhurst et al. | 606/232 |

Primary Examiner—Stephen C. Pellegrino
Assistant Examiner—Gary Jackson
Attorney, Agent, or Firm—Barnes & Thornburg

[57] ABSTRACT

An arrangement for attaching a suture to a bone includes a device which has an elongate body having first and second ends, a central portion, and a longitudinal axis extending through the ends. A suture is attached to the central portion of the body at a point which is offset from the longitudinal axis so that, when the device is placed in a hole in the bone and a force having a component acting in a direction which is parallel to the longitudinal axis of the device is applied to the suture, the device will rotate causing the ends to engage the bone and prevent removal of the device and suture from the hole. The ends of the device are preferably formed as sharp points. One embodiment is formed from a continuous length of stainless steel rod which is bent into a 360° loop. A novel method of using the device to secure a suture to a bone includes forming a hole which extends through a cortical layer of the bone and into a cancellous portion of the bone to a depth which at least equals the length of the device. The device and attached suture are inserted into the hole such that the outwardly facing end of the device is disposed inwardly of the inner cortical wall of the bone. Pulling the suture causes the device to rotate such that the ends penetrate the relatively soft cancellous portion of the bone and come to rest substantially adjacent the inner wall of the relatively hard cortical bone so as to secure the suture in place.

29 Claims, 2 Drawing Sheets

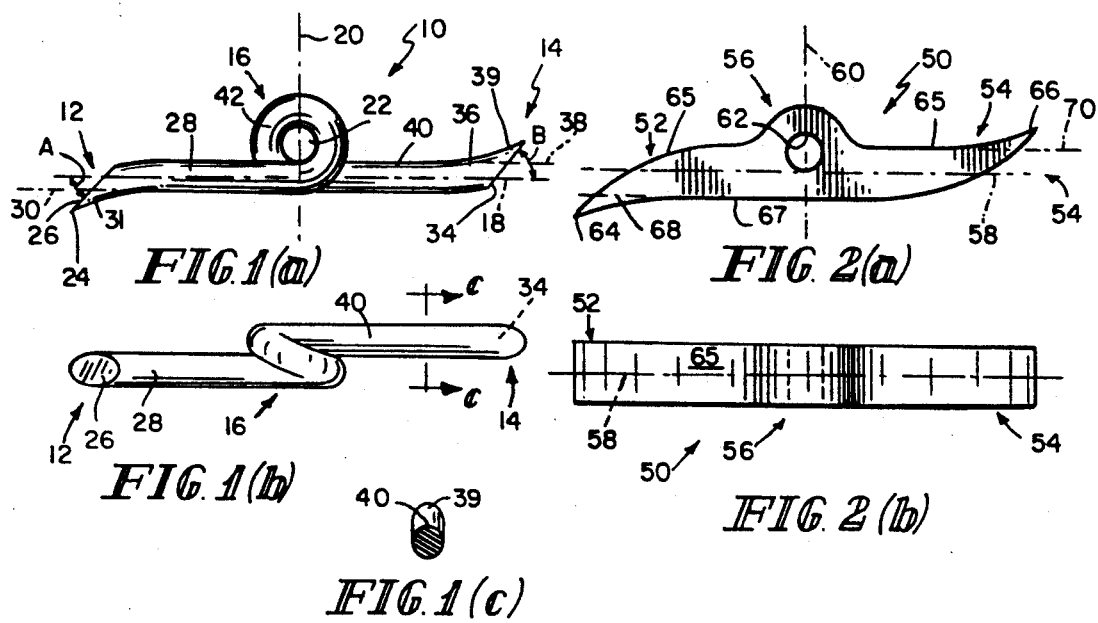
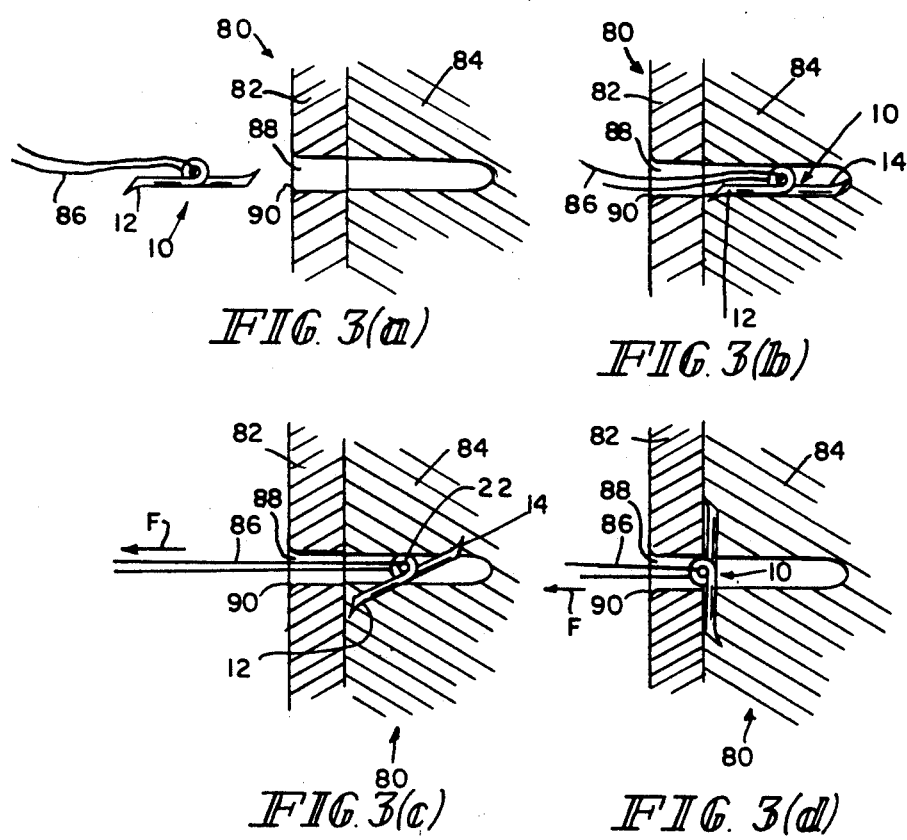

SUTURE RETAINING ARRANGEMENT

BACKGROUND AND SUMMARY OF THE INVENTION

This invention relates generally to surgical devices and, more particularly, to a device for attaching an object, such as a suture, to a bone, and to a method of using such a device.

Numerous devices are available to attach objects to bone. Several such devices are discussed in the background section of U.S. Pat. No. 4,898,156 to Gatturna et al. The Gatturna et al. patent describes a suture anchor which comprises a coupling member and an integrally formed barb. The coupling member comprises a generally cylindrical body which has a blind hole opening on one of its ends. A side slot communicates with the blind hole and terminates in an inclined surface intermediate the length of the coupling member. The barb comprises a curved length of material integrally formed on the opposite end of the coupling member which, in its unrestrained state, comprises an arc of approximately 90° of a loop approximately 0.250" in diameter. The barb is capable of being elastically deformed to a substantially straight configuration when desired. In its straightened configuration, the barb is preferably greater in length than the coupling member, as measured along the longitudinal axis.

The suture anchor of Gatturna et al. is intended to be utilized in conjunction with an installation tool which is shown in FIGS. 3-6 of the drawings. The installation tool comprises a hollow sheath and a plunger. To install a suture anchor, the anchor is forced into the interior bore of the sheath such that the barb is elastically deformed into its straight configuration. Initially, the suture anchor is left partially protruding from the sheath so that the blind hole in the end of the coupling member remains outside. A suture is attached to the coupling member by tying a knot in the end of the suture and slipping the knotted end of the suture into the blind hole and threading the body of the suture into the coupling member's side slot. Once the suture is so positioned, the suture and suture anchor assembly is pushed further into the installation tool so that the end of the coupling member is positioned substantially flush with the installation tool's front surface. Either before or after the suture anchor has been loaded into the installation tool and the suture attached to the anchor, an appropriately sized hole is formed in the bone to receive the suture and suture anchor assembly. The leading end of the installation tool is then inserted into the hole and the plunger is driven forward to eject the suture anchor out of the installation tool and into the hole. As the coupling member leaves the insertion tool and the barb approaches the mouth of the tool bore, the length of the barb is progressively released from the confines of the tool's bore, thereby allowing the barb to spring back to its normally curved position. This restoration of the barb's curved state causes the suture anchor to pivot on itself so that the anchor swings itself off-center and engages the bone at three different contact points.

Gatturna et al. state that the suture anchor and the receiving hole in the bone must be properly dimensioned relative to one another if the suture anchor is to properly and securely lodge itself in the hole. A specific relationship between the unconstrained suture anchor diameter, the constrained suture anchor diameter and the diameter of the hole is specified. This relationship requires that the barb be formed of a material which is simultaneously capable of substantial resilience and substantial strength. Modifications of the suture anchor which employ two, three or more barbs are also described.

The suture anchor described by Gatturna et al. is a relatively complex structure which, as noted, must be carefully formed and dimensioned in order to insure proper functioning. It is an object of the present invention to provide an alternative device for anchoring sutures to a bone, which device is relatively simple in design and structure and which is highly effective for its intended purpose.

Another object of the present invention is to provide a suture anchor which may be used to effectively retain sutures within a hole formed in a bone while avoiding the requirement of maintaining exact dimensional relationships between the device and the hole.

Yet another object of the present invention is to provide a novel method of securing a suture to a bone which utilizes the novel suture anchor now disclosed.

These and other objects are attained in a device for attaching an object, such as a suture, to a bone which comprises a relatively rigid elongate body having first and second ends and a central portion between said ends, and means for attaching a suture to the central portion of the body. The elongate body has a longitudinal axis which extends through the first and second ends. The suture is attached to the central portion of the body at a point which is offset from the longitudinal axis so that, when the device is placed in a hole in the bone and a force having a component acting in a direction which is parallel to the longitudinal axis of the device is applied to the suture, the device will rotate causing the ends of the elongate body to engage the bone and prevent removal of the device and suture from the hole. In a preferred embodiment, at least one of the ends of the elongate body is formed as a sharp point. The point is offset from the longitudinal axis and faces away from the axis and the central portion of the elongate body.

One embodiment of the invention is formed from a continuous length of rod-like material. The rod-like material has a generally circular cross-section and is formed in a loop which comprises the means for attaching the suture to the central portion of the body. In this embodiment, the sharp points are defined in part by cross-sectional surfaces of the ends which intersect the longitudinal axis to form acute angles. In a preferred embodiment, the angle formed by the intersection of each cross-sectional surface and the longitudinal axis is approximately 45°.

Another embodiment of the invention is machined, stamped or otherwise formed from stock material or powder metal. In this embodiment, an opening is formed in the central portion of the body through which the suture may be threaded. The embodiments described in detail below include "barb" structures formed on the ends for penetrating the bone and preventing removal of the device and suture from the hole.

The invention further comprises a method of securing a suture to a bone using a device of the type described above, which comprises the steps of: forming a hole which extends through a cortical layer of the bone and into a cancellous portion of the bone to a depth which at least equals the length of the elongate body of the device; inserting the device and attached suture into the hole such that the outwardly facing end of the device is disposed inwardly of an inner cortical wall of the bone; and pulling the suture to cause the device to rotate such that the ends of the device penetrate the relatively soft cancellous portion of the bone and come to rest substantially adjacent the inner wall of the relatively hard cortical bone so as to secure the suture in place.

Other objects, advantages and novel features of the present invention will become apparent from the following detailed description of the invention when considered in conjunction with the accompanying drawings.

BRIEF DESCRIPTION OF THE DRAWINGS

FIGS. 1(a) and 1(b) show side and top plan views, respectively, of a device which is constructed in accordance with the principles of the present invention. FIG. 1(c) is a cross-sectional view taken along line C—C of FIG. 1(b).

FIGS. 2(a) and 2(b) show side and top plan views, respectively, of another embodiment of a device which is constructed in accordance with the princples of the present invention.

FIGS. 3(a), 3(b), 3(c) and 3(d) illustrate a method of using the anchoring device of the present invention.

DETAILED DESCRIPTION OF THE DRAWINGS

Figure 4:
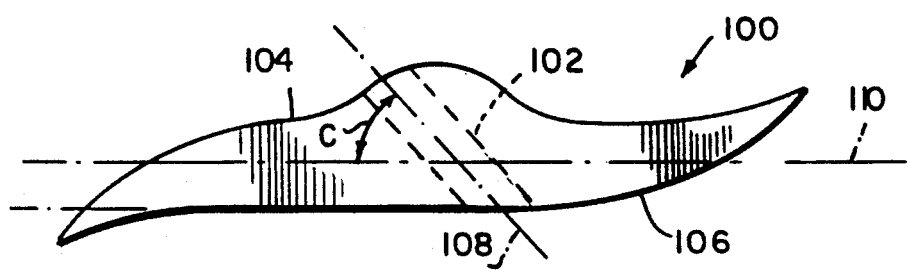
FIGS. 4(a) and 4(b) show side and top plan views, respectively, of another embodiment of a device constructed in accordance with the principles of the present invention.
Figure 4:
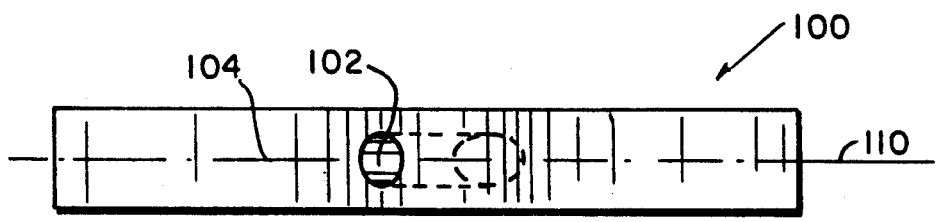

FIGS. 1(a) and 1(b) show side and top views, respectively, of an anchoring device 10 which is constructed in accordance with the present invention. Device 10 comprises an elongate body having a first end 12, a second end 14, and a central portion 16 disposed between first end 12 and second end 14. Also shown in FIG. 1(a) is a longitudinal axis 18 which extends through first and second ends 12 and 14, and a transverse axis 20 which intersects axis 18 at substantially right angles in the vicinity of central body portion 16.

Central body portion 16 includes an opening 22 which provides a means for attaching a suture to portion 16. Opening 22 is shown, in the embodiment illustrated, centered on transverse axis 20 and offset from longitudinal axis 18. The reason for locating opening 22 in offset relation to axis 18 is more fully discussed below.

First end 12 is formed to include a sharp point 24 which is offset from longitudinal axis 18, and which faces outwardly away from axis 18 and from central body portion 16. The degree to which point 24 is offset from axis 18 may vary. Point 24 is defined by the intersection of cross-sectional surface 26 and the outer, general)y cylindrical surface 28 of first end 12. Surface 26 intersects longitudinal axis 18 at an angle A of approximately 45°. Angle A may be increased or decreased from a relatively smaller to a relatively larger angle between 0+ and 90− degrees with corresponding impact upon the orientation of point 24.

In the vicinity of central portion 16, the outer peripheral surface 28 of device 10 extends substantially parallel to axis 18. However, in the vicinity of first end 12, surface 28 diverges from parallel relation with axis 18 in a direction which is generally opposite to the direction of offset from axis 18 of opening 22. This means that point 24 extends outwardly, relative to axis 18, further than it otherwise would, and beyond a plane defined by the peripheral edge of central body portion 16, as indicated by dashed line 30. This creates a "barb" 31 whose function is explained below in connection with FIGS. 3(a)–3(d).

Second end 14 is constructed similarly to first end 12, except that point 32 is offset from axis 18 in substantially the same direction as is opening 22. The degree to which point 32 is offset from axis 18 can also vary. Point 32 is defined by the intersection of cross-sectional surface 34 and the outer peripheral surface 36 of end 14. Angle B is approximately 45°. Point 32 extends beyond dashed line 38, which is an extension of the line defined by peripheral surface 40 of central body portion 16, to form "barb" 39.

Anchoring device 10 is formed from a continuous length of rod-like material which has been formed in a single 360° loop 42 in the vicinity of central portion 16. Loop 42 forms opening 22 which comprises means for attaching the suture to central portion 16 of device 10. The rod-like material used to form device 10 has a generally circular cross-section, as illustrated by FIG. 1(c) which is a cross-sectional view taken along line C—C of FIG. 1(b). Other cross-sectional shapes (e.g., rectangular) can be used. In one embodiment, the rod-like material from which device 10 is formed is stainless steel. However, other biocompatible materials having appropriate mechanical characteristics may be used.

FIGS. 2(a) and 2(b) show an alternative embodiment of the anchoring device of the present invention. Specifically, these figures show an anchoring device 50 which has a first end 52, a second end 54, a central portion 56, and a longitudinal axis 58 which extends through first and second ends 52 and 54. Anchoring device 50 also has a transverse axis 60 which intersects longitudinal axis 58 at substantially right angles. Centered on transverse axis 60, and offset from longitudinal axis 58 is through-opening 62 which provides a means for attaching a suture to central portion 56 of anchoring device 50. The reason for locating opening 62 in offset relation to longitudinal axis 58 is discussed below.

First and second ends 52 and 54 are provided with sharp points 64 and 66, respectively, which are disposed and oriented similarly to points 24 and 32 of anchoring device 10. Points 64 and 66 are formed by the intersection of surfaces 65 and 67 which extend in generally opposing relation longitudinally of device 50. Points 64 and 66 extend beyond dashed lines 68 and 70, respectively, to provide outwardly projecting "barbs" whose functions are also discussed in detail below.

Unlike anchoring device 10, which is formed from a continuous length of rod-like material, anchoring device 50 is molded, machined and/or stamped from a stock material or powdered metal. A preferred material is a titanium alloy (Ti-6Al-4V) having well-known biocompatibility characteristics.

FIGS. 3(a)–3(d) illustrate a preferred method of usage for anchoring devices 10 and 50. Each of these figures show a portion of bone tissue 80 which comprises an outer layer 82 of relatively hard cortical bone cells and an inner core 84 of relatively soft cancellous cells. A suture 86 is shown attached to (i.e., threaded through opening 22) device 10 which, in FIGS. 3(a), is positioned immediately adjacent bone tissue 80 prior to insertion. A hole 88 is formed in bone tissue 80, and extends through cortical layer 82 and into cancellous core 84. Hole 88 is preferably formed by drilling. A step drill which chamfers the outer edge 90 of hole 88 may be used, as is illustrated in FIGS. 23 and 24 of U.S. Pat. No. 4,899,743.

After hole 88 is formed, device 10 and suture 86 are inserted as illustrated in FIG. 3(b). An insertion tool of the type shown in U.S. Pat. Nos. 4,741,330; 4,898,156; or 4,899,743 may be used to insert device 10 into hole 88. Note that hole 88 extends into cancellous core 84 to a depth which is equal to or slightly greater than the overall length of device 10. Device 10 is oriented so that first end 12 is facing outwardly from hole 88. This means that sharp point 24 and "barb" portion 31 of end 12 are directly adjacent (and are preferably in contact with) the cancellous cells of core 84. When an outwardly directed force F is applied to suture 86, the offset positioning of opening 22, relative to first end 12, causes device 10 to rotate and barb 31 of first end 12 to dig into the cancellous cells of core 84, as illustrated in FIG. 3(c). As device 10 rotates, first end 12 and second end 14 penetrate core 84 as shown. Continued application of force F to suture 86 causes device 10 to assume its final placement immediately adjacent an interior wall 90 of cortical layer 82, as illustrated in FIG. 3(d).

FIGS. 4(a) and 4(b) show another embodiment, in the form of device 100, of a suture retainer which is constructed in accordance with the principles of the present invention. Device 100 is similar to device 50 of FIGS. 2(a) and 2(b), with the exception of the placement and direction of the through opening or passage provided through the central portion of the device. In the embodiment of FIGS. 4(a) and 4(b), passage 102 extends from top surface 104 through the central portion of the body to bottom surface 106. Passage 102 extends along an axis 108 which crosses longitudinal axis 110 to form an angle C of approximately 45°. In operation, the end of the suture is inserted into passage 102 and secured, by a knot or other means, adjacent bottom surface 106.

It should be readily apparent from the materials specified and from the method of intended usage discussed above that anchoring devices 10, 50 and 100 are relatively rigid devices. While it may be possible to accommodate some resilience and to form the devices from plastics or other relatively resilient materials, no resilience or flexibility is required for purpose of installation or proper functioning of the devices of the present invention. In addition to the materials specified above, the subject anchoring devices may also be made of plastic, polymers (either resorbable or non-resorbable), bioceramics, ceramics and other suitable materials.

Anchoring devices 10 and 50 may be modified without departing from the spirit of the present invention. For example, formation of the "barb" structures referred to above may not be necessary if adequate penetration of the cancellous portion of the bone may be achieved by alternative structures (i.e., sharp points, knife edges, etc.). The barb structure may be included on the first end of the device (i.e., the end facing outwardly from the hole in the bone), but omitted from the second end (i.e., the end which is inserted into the hole first). Alternatively, a barb which is substantially identical in orientation to that formed on the first end of the device may be provided on the second end as well so that the device may be inserted into the hole without regard as to which end faces outwardly from the hole. Other modifications will no doubt be apparent to those skilled in this art.

From the preceding description of the preferred embodiments, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. A device for attaching an object such as a suture to a bone, comprising:
    a relatively rigid, elongate body having first and second ends, a central portion between said ends, and a longitudinal axis extending through said ends; and
    means for attaching a suture substantially midway between the first and second ends of the body at a point which is offset from the longitudinal axis so that, when the device is placed in a hole in the bone and a force having a component acting in a direction which is parallel to the longitudinal axis of the device is applied to the suture, the device will rotate causing the ends to engage the bone and prevent removal of the device and suture from the hole;
    wherein at least one of said first and second ends is formed as a sharp point and wherein said sharp point is offset from the longitudinal axis, and faces away from said axis and the central portion of the elongate body.

2. A device according to claim 1, wherein said sharp point is defined in part by a cross-sectional surface of said end, and wherein said surface intersects the longitudinal axis to form an acute angle.

3. A device according to claim 2, wherein said angle is approximately 45°.

4. A device according to claim 2, wherein said sharp point is defined by the intersection of said cross-sectional surface and an outer peripheral surface of the elongate body.

5. A device according to claim 4, wherein said outer peripheral surface extends in substantially parallel relation to the longitudinal axis between the central and end portions, but extends away from said axis in the vicinity of said intersection to define a point which faces away from the longitudinal axis and the central portion of the elongate body.

6. A device according to claim 1, wherein said point is defined by the intersection of opposing surfaces which extend longitudinally of the device.

7. A device according to claim 6, wherein said means for attaching a suture to the central portion of the body comprises a passage extending through said body and opening onto each of said opposing surfaces.

8. A device according to claim 7, wherein said passage extends generally transversely of the body and intersects the longitudinal axis to form an acute angle.

9. A device according to claim 8, wherein said acute angle is approximately 45°.

10. A device according to claim 1, wherein both of said first and second ends are formed as sharp points.

11. A device according to claim 10, wherein said points are offset from said longitudinal axis, and face away from said axis and the central portion of the elongate body, and face in generally opposing directions.

12. A device according to claim 1, wherein said elongate body is formed from a continuous length of rod-like material.

13. A device according to claim 12, wherein said continuous length of rod-like material is formed in a loop at the central portion of the body, and wherein said loop comprises said means for attaching the suture to the central portion of the body.

14. A device according to claim 12, wherein said rod-like material has a generally circular cross-section.

15. A device for anchoring a suture to a bone or similar structure, comprising:
 an elongate body having first and second ends, a central portion between said ends, a longitudinal axis extending through each of said ends, and a transverse axis extending through the central portion of the body and intersecting the longitudinal axis at substantially right angles; and
 means for attaching the suture substantially midway between the first and second ends of the body at a point along the transverse axis which is offset from the longitudinal axis;
 wherein said first end is formed as a point which is offset from the longitudinal axis in generally opposing relation to the means for attaching the suture.

16. A device according to claim 15, wherein said point faces away from the longitudinal axis and the central portion of the elongate body.

17. A device according to claim 15, wherein said point extends outwardly from the longitudinal axis beyond an adjacent sidewall of the central portion of the elongate body.

18. A device according to claim 15, wherein said second end is formed as a point which is offset from the longitudinal axis in generally opposing relation to the point formed on said first end.

19. A device according to claim 18, wherein said point on the second end extends outwardly from the longitudinal axis beyond an adjacent sidewall of the central portion of the elongate body.

20. A device according to claim 15, wherein said means for attaching the suture to the central portion of the body comprises an opening formed in the central portion of the body.

21. A device according to claim 15, wherein said body is formed of a continuous length of rod-like material.

22. A device according to claim 21, wherein said means for attaching the suture to the central portion of the body comprises an opening formed by bending the rod-like material into a 360° loop.

23. A device according to claim 15, wherein said elongate body is formed as a relatively rigid structure.

24. A device for anchoring a suture to a bone or similar structure, comprising:
 an elongate body having first and second ends, a central portion between said ends, a longitudinal axis extending through each of said ends, and a transverse axis extending through the central portion of the body and intersecting the longitudinal axis at an acute angle; and
 means for attaching the suture to the central portion of the body, said means comprising a passage which extends through said body and coaxially with said transverse axis, said passage defining two openings on substantially opposite sides of the body;
 wherein said first end is formed as a point which is offset from the longitudinal axis in generally opposing relation to the nearer of said two openings.

25. A device according to claim 24, wherein said second end is formed as a point which is offset from the longitudinal axis in generally opposing relation to the other of said two openings.

26. A device according to claim 24, wherein said acute angle is approximately 45°.

27. A method of securing a suture to a bone using a device which comprises an elongate body having first and second ends, a central portion between said first and second ends, and means for attaching the suture to the central portion at a point which is offset from a longitudinal axis which extends through the first and second ends, comprising the steps of:
 a. forming a hole which extends through a cortical layer of the bone and into a cancellous portion of the bone to a depth which at least equals a length of the elongate body of the securing device;
 b. inserting the device and attached suture into the hole such that the outwardly facing end of the device is disposed inwardly of an inner cortical wall of the bone; and
 c. pulling the suture to cause the device to rotate such that the first and second ends penetrate the relatively soft cancellous portion of the bone and come to rest substantially adjacent the inner wall of the relatively hard cortical bone so as to secure the suture in place.

28. A method of securing a suture to a bone using a device which comprises an elongate body having first and second ends, a central portion between said first and second ends, a sharp point on said first end, and means for attaching the suture to the central portion at a point which is offset from a longitudinal axis which extends through the first and second ends, comprising the steps of:
 a. forming a hole in the bone having a depth which at least equals a length of the elongate body of the securing device;
 b. inserting the device and attached suture into the hole; and
 c. pulling the suture to cause the device to rotate and the sharp point to penetrate the bone so as to prevent the device and suture from being removed from the hole.

29. In combination, a suture and a device for attaching the suture to a bone, comprising:
 a relatively rigid, elongate body having first and second ends, a central portion between said ends, and a longitudinal axis extending through said ends, at least one of said first and second ends being adapted to engage the bone; and
 means for attaching the suture substantially midway between the first and second ends of the body at a point which is offset from the longitudinal axis so that, when the device is placed in a hole in the bone and a force having a component acting in a direction which is parallel to the longitudinal axis of the device is applied to the suture, the device will rotate causing the end to engage the bone and prevent removal of the device and suture from the hole.

* * * * *